United States Patent [19]

Nifant'ev et al.

[11] Patent Number: 5,968,863
[45] Date of Patent: Oct. 19, 1999

[54] PROCESS FOR THE PREPARATION OF BRIDGED METALLOCENES

[75] Inventors: Ilya E. Nifant'ev; Pavel V. Ivchenko, both of Moscow, Russian Federation; Luigi Resconi, Ferrara, Italy

[73] Assignee: Montell Technology Company B.V., Netherlands

[21] Appl. No.: 08/599,476

[22] Filed: Jan. 23, 1996

[30] Foreign Application Priority Data

Jan. 23, 1995 [IT] Italy .................................. MI95A0098

[51] Int. Cl.$^6$ ............................... B01J 31/00; C07F 7/24; C07F 7/08; C07F 7/04

[52] U.S. Cl. ............................... 502/104; 556/11; 556/53; 556/95; 556/431; 556/489

[58] Field of Search ............................... 502/104; 556/11, 556/53, 95, 431, 489

[56] References Cited

U.S. PATENT DOCUMENTS

| | | |
|---|---|---|
| 4,769,510 | 9/1988 | Kaminsky et al. . |
| 5,103,030 | 4/1992 | Rohrmann et al. . |

FOREIGN PATENT DOCUMENTS

| | | |
|---|---|---|
| 2104036 | 2/1994 | Canada . |
| 0 316 155 A2 | 5/1989 | European Pat. Off. . |
| 0 320 762 A3 | 6/1989 | European Pat. Off. . |
| 0 530 908 | 3/1993 | European Pat. Off. . |
| 0 643 078 | 3/1995 | European Pat. Off. . |
| WO 95/09172 | 4/1995 | WIPO . |
| WO 95/35333 | 12/1995 | WIPO . |

OTHER PUBLICATIONS

Organometallics, 1991, 10, 1501–1505.
Organometallics, 1992, 11, 2115–2122.
Chemical Abstracts, vol. 117, No. 25, , Abstract No. 251465j, 1992.
Chemical Abstracts, vol. 117, No. 14, Abstract No. 131610d, 1992.
Chemical Abstracts, vol. 115, No. 17, Abstract No. 183466s, 1991.
Chemical Abstracts, vol. 123, No. 17, Abstract No. 123:228383w, 1995.
Nifant'ev, I.E., et al, Organometallics, 1991, 10, pp. 3739–3745, 1991.
Coughlin, E.B., et al, J. Am. Chem. Soc., 1992, 114, pp. 7606–7607, 1992.

*Primary Examiner*—John Kight
*Assistant Examiner*—Raymond Covington
*Attorney, Agent, or Firm*—Bryan Cave LLP

[57] ABSTRACT

It is possible to prepare in high yield and purity the racemic and meso forms of bridged chiral metallocenes with a stereoselective method, by synthesizing the sylil-, germyl- or stannyl-substituted ligands. These compounds can be prepared in their racemic and meso forms, and then selectively transformed in the corresponding metallocenes.

29 Claims, No Drawings

PROCESS FOR THE PREPARATION OF BRIDGED METALLOCENES

The present invention relates to a process for the preparation of bridged metallocene compounds as well as to bridged bis-cyclopentadienyl ligands.

Stereorigid metallocene compounds having two substituted cyclopentadienyl ligands joined by means of a bridging group which gives stereo-rigidity to the molecule are known to be stereospecific catalyst components for the preparation of isotactic polyolefins. These metallocenes can exist in two configurations, that is the racemic and the meso isomeric form. As the chiral racemic form only is stereospecific, the meso form is generally removed by separation from the rac/meso mixtures obtained from the metallocene synthesis.

Thus, for example, in U.S. Pat. No. 4.769.510 it is described the use of rac-ethylene-bis(indenyl)zirconium dichloride and of rac-ethylene-bis(4,5,6,7-tetrahydroindenyl)zirconium dichloride in combination with methylalumoxane for the preparation of isotactic polypropylene.

The ethylene-bis(indenyl)zirconium dichloride can be prepared according to the method described in "Organometallics, 1991, 10, 1501–1505" wherein an about 2:1 rac/meso mixture is obtained with 75% yield, or according to the method described in "Organometallics, 1992, 11, 2115–2122" wherein the yield is 52% of the pure racemic isomer.

An improvement of the method for preparing a bridged metallocene is described in the European patent application EP-530,908 wherein a liquid dispersant which is a weak Lewis base, such as an ether, is used. In the working examples ethylene-bis(indenyl)zirconium dichloride about 1:1 rac/meso was prepared with a yield higher than 95%, or the pure racemic isomer was obtained with a yield of 65%.

It is also known that stereorigid metallocene compounds of the above type in their meso isomeric form can be used in catalyst systems for the preparation of high molecular weight ethylene polymers (EP-643,078).

Mixtures of racemic and meso isomers of a stereorigid metallocene in fixed ratios can be suitably used to prepare ethylene copolymers having uniform distribution of the comonomeric units along the polymeric chain, together with a wide molecular weight distribution (PCT/EP95/02372).

It would be highly desirable to be able to prepare each of the racemic or meso isomeric form of these metallocene compounds in high yields and with high purities, or rac/meso mixtures in the desired ratios, thus avoiding long, impractical and expensive purification operations.

Therefore, an object of the present invention is a process for the preparation of a bridged metallocene compound in the racemic or meso isomeric form, or as a mixture of the racemic and meso isomeric forms, said process comprising the following steps:

(a) reacting a ligand having two substituted and bridged cyclopentadienyl groups with a compound able to form a delocalized anion on each of the cyclopentadienyl groups, thus obtaining the corresponding double anion;

(b) reacting the double anion with a compound of formula $ZR_3Q$ or $(ZR_2)_mQ_2$, wherein Z is a silicon, germanium or tin atom, R is a hydrocarbon group containing from 1 to 10 carbon atoms, Q is an halogen atom, m is 1 or 2, thus obtaining a mixture of the racemic and meso isomeric forms of a Z-substituted bridged bis-cyclopentadienyl ligand;

(c) if desired, separating at least part of one of the isomeric forms of the Z-substituted bridged bis-cyclopentadienyl ligand; and (d) converting the Z-substituted bridged bis-cyclopentadienyl ligand into the desired product through reaction with a transition metal compound, the reaction being carried out in a liquid dispersant which does not coordinate with the transition metal compound.

Bridged and substituted bis-cyclopentadienyl ligands suitable for use as starting compounds in the process of the present invention are those of formula (I):

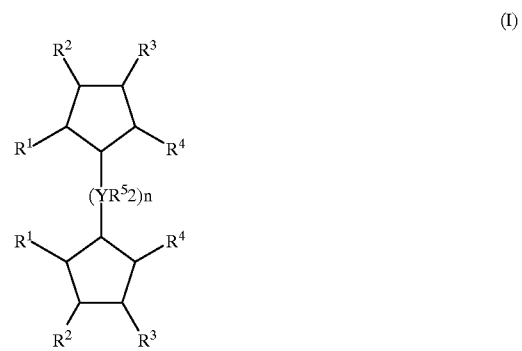

(I)

wherein, on each cyclopentadienyl group, the $R^1$, $R^2$, $R^3$ and $R^4$ substituents, same or different, are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals and can contain Si or Ge atoms, and moreover two of the $R^1$, $R^2$, $R^3$ and $R^4$ substituents adjacent on the same cyclopentadienyl ring can form a cycle comprising from 5 to 8 carbon atoms, with the proviso that, in at least one cyclopentadienyl group, $R^1$ is different from $R^4$ or $R^2$ is different from $R^3$;

Y is a carbon, silicon or germanium atom;

the $R^5$ substituents, same or different, are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals or $C_7$–$C_{20}$ arylalkyl radicals, and moreover two substituents $R^5$ can form a cycle comprising from 4 to 8 carbon atoms;

n is an integer comprised between 1 and 4, preferably being 1 or 2.

The double bonds of the cyclopentadienyl rings in the compounds of formula (I) can be in any of the allowed positions.

When in the bridged bis-cyclopentadienyl ligand of formula (I) Y is a silicon atom, in the compound of formula $ZR_3Q$ or $(ZR_2)_mQ_2$ Z is a germanium or tin atom.

When in the bridged bis-cyclopentadienyl ligand of formula (I) Y is a germanium atom, in the compound of formula $ZR_3Q$ or $(ZR_2)_mQ_2$ Z is a tin atom.

Non limitative examples of bis-cyclopentadienyl ligands useable in the process of the invention are:

| | | | |
|---|---|---|---|
| Me$_2$C(Me-Cp)$_2$ | Me$_2$C(Et-Cp)$_2$ | Me$_2$C(i-Pr-Cp)$_2$ | Me$_2$C(t-Bu-Cp)$_2$ |
| C$_2$H$_4$(Ind)$_2$ | C$_2$H$_4$(H$_4$Ind)$_2$ | Me$_2$Si(Ind)$_2$ | |
| Me$_2$Si(H$_4$Ind)$_2$ | | | |
| Me$_2$C(Ind)$_2$ | Me$_2$C(H$_4$Ind)$_2$ | Me$_2$C(3-Me$_3$-Ind)$_2$ | |
| Ph(Me)Si(Ind)$_2$ | Ph$_2$Si(Ind)$_2$ | C$_2$Me$_4$(Ind)$_2$ | Me$_2$SiCH$_2$(Ind)$_2$ |
| C$_2$H$_4$(2-MeInd)$_2$ | C$_2$H$_4$(4,7-Me$_2$Ind)$_2$ | C$_2$H$_4$(5,6-Me$_2$Ind)$_2$ | |
| C$_2$H$_4$(2,4,7-Me$_3$Ind)$_2$ | C$_2$H$_4$(2-MeH$_4$Ind)$_2$ | C$_2$H$_4$(4,7-Me$_4$H$_4$Ind)$_2$ | |
| C$_2$H$_4$(2,4,7-Me$_3$H$_4$Ind)$_2$ | Me$_2$Si(2-MeInd)$_2$ | Me$_2$Si(4,7-Me$_2$Ind)$_2$ | |
| Me$_2$Si(5,6-Me$_2$Ind)$_2$ | Me$_2$Si(2,4,7-Me$_3$Ind)$_2$ | Me$_2$Si(2-MeH$_4$Ind)$_2$ | |
| Me$_2$Si(4,7-Me$_2$H$_4$Ind)$_2$ | Me$_2$Si(2,4,7-Me$_3$H$_4$Ind)$_2$ | | | wherein Me=methyl, Et=ethyl, Pr=propyl, Bu=buthyl, Ph=phenyl, Cp=cyclopentadienyl, Ind=indenyl, H$_4$Ind=4,5,6,7-tetrahydroindenyl.

Compounds able to form a delocalized anion that can be used in step (a) of the process of the invention are, for example:

- organometallic compounds of alkali or earth-alkali metals, particularly alkyl-lithium compounds, such as methyl-lithium and n-butyl-lithium;
- metal hydrides, such as potassium hydride;
- alkali or earth-alkali metals, particularly metallic sodium or potassium;
- amides of alkali or earth-alkali metals, particularly sodium or potassium amide.

In the compound of formula ZR$_3$Q or (ZR$_2$)$_m$Q$_2$, Z is preferably a silicon atom, Q is preferably a chlorine atom and R is preferably an alkyl group containing from 1 to 3 carbon atoms.

Non limitative examples of compounds of formula ZR$_3$Q that can be used in step (b) of the process of the invention are: (CH$_3$)$_3$SiCl, ((C$_2$H$_5$)$_3$SiCl, (CH$_3$)$_3$SnCl, (C$_2$H$_5$)$_3$SnCl.

Non limitative examples of compounds of formula (ZR$_2$)$_m$Q$_2$ that can be used in step (b) of the process of the invention are: (CH$_3$)$_2$SiCl$_2$, (C$_2$H$_5$)$_2$SiCl$_2$, [(CH$_3$)$_2$Si]$_2$Cl$_2$, (CH$_3$)$_2$SnCl$_2$, (C$_2$H$_5$)$_2$SnCl$_2$, [(CH$_3$)$_2$Sn]$_2$Cl$_2$.

Transition metal compounds that can be used in the reaction of step (d) of the process of the invention are, for example, those of transition metals belonging to the group 3, 4, 5 or 6 or to the Lanthanides or Actinides group of the Periodic Table of the Elements (new IUPAC version).

Transition metal compounds particularly suitable for use in the reaction of step (d) of the process of the invention are the compounds of formula MX$_4$, wherein M is a titanium, zirconium or hafnium atom and X is an halogen atom.

Non limitative examples of compounds of formula MX$_4$ are titanium tetrachloride, zirconium tetrachloride and hafnium tetrachloride.

The reaction between the Z-substituted bridged ligand and the transition metal compound of step (d) has to be carried out in a liquid dispersant which does not coordinate with the transition metal compound.

Non limitative examples of said liquid dispersants are: dichloromethane, trichloromethane, benzene, toluene, xylene, pentane, n-hexane, cyclohexane.

The product obtained from the reaction of step (b) consists of a rac/meso mixture of the Z-substituted bridged bis-cyclopentadienyl ligand.

It is another object of the present invention a bridged bis-cyclopentadienyl ligand of formula (II):

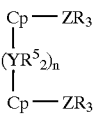

(II)

or of formula (III):

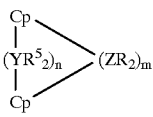

(III)

wherein each Cp is a substituted cyclopentadienyl ring, and R$^5$, Y, Z, R, m and n are defined as above, in its racemic or meso isomeric form.

In the bridged bis-cyclopentadienyl ligand of formula (II) or (III) Z is preferably a silicon atom. Particularly interesting bridged bis-cyclopentadienyl ligand of formula (II) are 1,2-bis(1-trimethylsilyl-indenyl)ethane, 1,2-bis(1-trimethylsilyl-4,7-dimethyl-indenyl)ethane and 2,2-bis(1-trimethylsilyl-indenyl)propane in their racemic or meso isomeric form.

The two isomeric forms of the Z-substituted bridged bis-cyclopentadienyl ligand are generally stable and can be separated one from the other by the common separation methods such as, for example, fractionated crystallization and extraction with solvents.

The said separation methods are carried out under conventional crystallization conditions.

Non limitative examples of solvents which can be used for the above separation process are hydrocarbons such as pentane and hexane, as well as mixtures thereof.

Thus, with the process of the present invention it is possible to prepare a bridged metallocene compound of formula (IV):

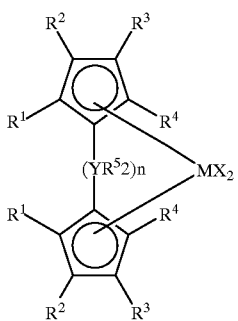

(IV)

where $R^1$, $R^2$, $R^3$, $R^4$, $R^5$, Y, M, X and n are defined as above, in its pure racemic or meso isomeric form.

The X substituents in the metallocene compounds obtainable by the process of the invention can be substituted with X' substituents which are hydrogen atoms, $R^6$, $OR^6$, $SR^6$, $NR^6_2$ or $PR^6_2$ groups, wherein substituents $R^6$, same or different from each other, are $C_1-C_{20}$ alkyl radicals, $C_3-C_{20}$ cycloalkyl radicals, $C_2-C_{20}$ alkenyl radicals, $C_6-C_{20}$ aryl radicals, $C_7-C_{20}$ alkylaryl radicals or $C_7-C_{20}$ arylalkyl radicals and can contain Si or Ge atoms.

The substitution reaction of substituents X with substituents X' can be carried out by generally used methods. For example, when the desired substituents X' are alkyl groups, the metallocene compound can be reacted with alkylmagnesium halides (Grignard reagents) or with lithioalkyl compounds.

According to a particular embodiment of the process of the invention, the reaction of step (a) is suitably performed by adding a solution of an organic lithium compound in an aprotic solvent to a solution of the bridged ligand in an aprotic solvent.

Thus, a solution containing the double anion of the bridged ligand is obtained, and this is added to a solution of the compound of formula $ZR_3Q$ or $(ZR_2)_mQ_2$ in an aprotic solvent to perform the reaction of step (b).

Non limitative examples of aprotic solvents suitable for use in steps (a) and (b) of the present process are tetrahydrofurane, dimethoxyethane, diethylether, benzene, toluene, xylene, dichloromethane, trichloromethane, pentane, n-hexane, cyclohexane, the diethylether being the preferred.

The rac/meso mixture of the Z-substituted bridged ligand obtained from the reaction of step (b) can be subjected to a separation process in order to remove part or all of the undesired isomer.

Then, the desired isomer, or mixture of isomers, of the Z-substituted bridged ligand is allowed to react with the metal compound to give the corresponding metallocene. This reaction can be suitable performed in dichloromethane. Once recovered the product, the reaction medium can suitably be recycled.

The temperature and pressure conditions for the whole process are not critical. They depend on the used solvents, the only requirement being that the system is in the liquid state.

The metallocenes which can be prepared by the process of the present invention are useable, in combination with a cocatalyst, in the polymerization of olefins.

The following examples are given for illustrative purposes and do not limit the invention.

CHARACTERIZATIONS

The $^1$H-NMR analyses were carried out on a Bruker 200 MHz instrument, using $CDCl_3$ as a solvent, at room temperature.

All the operations were carried out in a dry nitrogen atmosphere, using the conventional techniques for the handling of compounds which are sensitive to air.
THF=tetrahydrofuran
$Et_2O$=ethyl ether
DME=dimethoxyethane

EXAMPLE 1 rac- and mesco-ethylene-bis(indenyl)zirconium dichloride from bis(1-trimethylsilyl-indenyl)ethane in $CH_2Cl_2$ (a) Synthesis of bis(1-trimethylsilyl-indenyl)ethane Bis-indenyl-ethane (11.35 g) was dissolved with 300 ml of THF in a 500 ml flask under nitrogen. To the resulting yellow solution, 58 ml of a 1.6 M $Et_2O$ solution of MeLi were added dropwise at room temperature with stirring. After the addition was complete, the orange solution was stirred for two hours.

In a 1 L flask were placed 100 ml THF and 13.5 ml of TMSCl, the solution was cooled to 0° C. and to it the previous solution of the dilithium salt of bisindenylethane was added dropwise over two hours with stirring while keeping the temperature at 0° C. After the addition was complete, the solution was allowed to warm to room temperature (after 1,5 h the solution turned yellow) and stirred three days. 5 ml of water were added, the solvents removed in vacuo to leave a light brown paste which was taken up in 100 ml $CH_2Cl_2$. The slurry was filtered, the solution dried over $Na_2SO_4$ and concentrated in vacuo to yield 16.9 g of a light brown solid which consists of a 1:1 rac:meso mixture of bis(1-trimethylsilyl-indenyl)ethane (yield 95.7%, GC purity 98.9%).

(b) Synthesis of rac- and meso-ethylene-bis(indenyl) zirconium dichloride 8.66 g of $ZrCl_4$ and 100 ml $CH_2Cl_2$ were placed in a 100 ml flask. In a second 100 ml flask, 14.96 g of bis(1-trimethylsilyl-3-indenyl)ethane were dissolved in 100 ml $CH_2Cl_2$. The two mixtures were slowly (5 ml every 30') and simultaneously added into a 500 ml flask containing 200 ml of rapidly stirring $CH_2Cl_2$. A red-brown slurry is obtained, which was stirred overnight and then concentrated in vacuo to a volume of 100 ml. 300 ml of $Et_2O$ were added, the mixture stirred and then filtered. The bright yellow solid was dried in vacuo (7.96 g). The solution was further concentrated to give additional yellow powder which was filtered and added to the first crop. The combined solids were washed with $CH_2Cl_2$ (2×20 ml) and then dried in vacuo to yield 8.63 g (55.5%) of bright yellow, chemically pure ethylenebis(indenyl)$ZrCl_2$ as a 1:1 mixture of its racemic and meso isomers.

EXAMPLE 2 rac- and meso-ethylene-bis(indenyl)zirconium dichloride from bis (1-trimetllylstannyl-indenyl) ethane in toluene 5.40 g (20 mmol) of dilithio-1,2-bis(inden-1-yl)ethane was suspended in 100 ml of ether, cooled up to −20° C., and treated with 8.76 g (44 mmol) of $Me_3SnCl$. The organic layer was separated, evaporated, and mixed with 50 ml of toluene. 4.66 g (20 mmol) of $ZrCl_2$ was added, and the mixture was stirred for 6 h under 80° C. Toluene was removed, the crude product was washed with 3×50 ml ether. 8.03 g of the mixture of rac- and meso-forms (1:1) was obtained (yield 96%). Pure rac-isomer was isolated with the yield of 45% by washing with 3×50 ml of DME under 80° C.

EXAMPLE 3 rac-ethylene-bis(indenyl)zirconium dichloride from rac-bis(1-trimethylsilyl-indenyl)ethane in $CH_2Cl_2$ 5.40 g (20 mmol) of dilithio-1,2-bis(inden-1-yl)ethane was suspended in 100 ml of ether, cooled to −20° C., and treated with 4.78 g (44 mmol) of $Me_3SnCl$. The organic layer was separated, evaporated, and 30 ml of pentane was added. Rac-form of bis(trimethylsilyl-inden-1-yl)ethane was isolated by crystallization as a white powder with a yield of 3.38 g (42%). This compound was mixed with 50 ml of $CH_2Cl_2$. 1.96 g (8.4 mmol) of $ZrCl_4$ was added, and the mixture was stirred for 12 h at 60° C. The solvent was removed, the crude product was washed with 3×10 ml THF (0° C.). 2.95 g of pure rac-form was obtained (yield 84%).

EXAMPLE 4 (COMPARISON)

rac- and meso-ethylene-bis(indenyl)zirconium dichloride from bis(1-trimethylstannyl-indenyl) ethane in THF It was worked as in Example 2, but using 50 ml of THF instead of toluene. No product was obtained.

EXAMPLE 5 (COMPARISON)

rac- and meso-ethylene-bis(indenyl)zirconium dichloride from bis(1-trimethylstannyl-indenyl) ethane in $Et_2O$ It was worked as in Example 2, but using 75 ml of $Et_2O$ instead of toluene and keeping the mixture stirred for 48 hours at 50° C. No product was obtained.

EXAMPLE 6 rac-isopropylidene-bis(indenyl)zirconium dichloride from the trimethylstannyl-derivative in toluene 5.45 g (20 mmol) of 2,2-bis(indenyl)propane was dissolved in 100 ml of ether. The thus obtained solution was cooled to −20° C. and treated with 22 ml of a 2.0M solution of n-BuLi in pentane. The resulting suspension was allowed to warm to room temperature, then it was cooled to −40° C. and treated with 12.06 g (50 mmol) of triethylstannylchloride. The organic layer was separated, evaporated, and mixed with 50 ml of toluene. 4.66 g (20 mmol) of $ZrCl_4$ was added, and the mixture was heated to 80° C. and stirred for 6 hours. Toluene was removed and the product was washed with DME (5×50 ml). 3.98 g of pure rac-isopropylidene-bis (indenyl)zirconium dichloride was obtained. (yield 46%).

EXAMPLE 7 rac-isopropylidene-bis (3-trimethylsilyl-indenyl) zirconium dichloride from the triethylstannyl-derivative in toluene It was worked as in Example 6, but using 8.34 g (20 mmol) of 2,2-bis(3-trimethylsilyl-indenyl)propane instead of 2,2-bis(indenyl)propane and recrystallizing the product from DME. 3.69 g of pure rac-form was obtained (yield 32%).

EXAMPLE 8 rac- and meso-isopropyliden-bis(3-isopropylcyclopentadienyl)zirconium dichloride from the triethylstannyl-derivative in toluene It was worked as in Example 6, but using 5.45 g (20 mmol) of the dilithium salt of 2,2-bis(3-isopropylcyclopentadienyl)propane instead of 2,2-bis (indenyl)propane and recrystallising the product from ether. 6.06 g (72%) of the mixture of rac- and meso- forms (1:1) was obtained.

EXAMPLE 9 rac-isopropyliden-bis (3-t-butyl-cyclopentadienyl) zirconium dichloride from the triethylstannyl-derivative in toluene It was worked as in Example 6, but using 6.01 g (20 mmol) of 2,2-bis(3-t-butyl-cyclopentadienyl)propane instead of 2,2-bis(indenyl)propane and washing the product with 50 ml of pentane and then recrystallizing it from ether. 1.97 g (22%) of pure rac-form was obtained.

EXAMPLE 10

Isopropylidene(cyclopentadienyl)(indenyl) zirconium dichloride from the triethylstannyl-derivative in toluene (a) Synthesis of 2,2-(cyclopentadienyl)(indenyl)propane 15 g of the milled KOH and 23.5 ml (200 mmol) of indene were suspended in 150 ml of DME and the mixture was heated to reflux. Then 24.1 ml (200 mmol) of 6,6-dimethylfulvene was added dropwise within 0.5 h and the mixture was stirred under reflux in additional 0.5 h. After that, the mixture was cooled, treated by 200 ml of water and by 100 ml of diethyl ether. The organic layer was separated, washed by water and dried by $CaCl_2$. Then the solvent was removed in vacuo and the residue was distilled, collecting the fraction boiling between 100 and 130° C./0.02 torr. 62.3 g of the product was obtained as a pale-yellow oil which was used without purification (yield 56%). $^1$H-NMR (acetone-d6; 30° C.) d: 7.36–7.18; 7.03; 6.39–6.21 (mm, 8H) 3.22; 2.90; 2.69 (mm, 4H) 1.55; 1.54 (s, 6H). $^{13}$C-NMR (acetone-d6; 30° C.) d: 156.3; 153.8; 151.7; 150.9; 145.1; 145.0; 143.9; 143.8 (quat.) 133.2; 133.1; 131.6; 130.9; 125.8; 126.3; 125.5; 125.5; 125.4; 125.3; 123.9; 123.9; 123.6; 123.5; 121.8; 121.6 (tert.) 40.8; 40.6; 36.8; 36.75 (—$CH_2$—) 38.0; 37.2 (>C<) 28.5; 27.5 (—$CH_3$).

(b) Synthesis of isopropylidene(cyclopentadienyl)(indenyl) zirconium dichloride 4.45 g (20 mmol) of 2,2-(cyclopentadienyl)(indenyl) propane was dissolved in 100 ml of ether, cooled up to −20° C., and treated by 22 ml of 2.0M n-BuLi/pentane. The resulting suspension was allowed to warm to room temperature, then cooled to −40° C., and treated with 12.06 g (50 mmol) of $Et_2SnCl$. Organic layer was separated, evaporated, and mixed with 50 ml of toluene. 4.66 g (20 mmol) of $ZrCl_4$ was added, and the mixture was stirred for 6 hours under 80° C. Toluene was removed, the crude product was recrystallized from THF. 5.97 g of the product was obtained (yield 78%).

EXAMPLE 11

Isopropylidene(cyclopentadienyl)(indenyl)titanium dichloride from the dimethylstannyl-derivative in toluene 5.56 g (20.5 mmol) of 2,2-(cyclopentadienyl)(indenyl) propane was dissolved in 100 ml of ether, cooled to −20° C., and treated with 22 ml of 2.0M n-BuLi/pentane. The resulting suspension was allowed to warm to room temperature, then cooled to −40° C., and treated with 9.89 g (45 mmol) of $Me_2SnCl_2$ and stirred for additional 6 h. The organic layer was separated, evaporated, and mixed with 50 ml of toluene.

2.25 ml (20.5 mmol) of TiCl$_4$ was added, and the mixture was stirred for 1 h under 80° C. Toluene was removed, crude product was recrystallized from THF and washed by 3×20 ml of ether. 2.22 g of the product was obtained (yield 32%). $^1$H-NMR (CD$_2$Cl$_2$; 30° C.) d: 7.60 (m, 2H); 7.45 (m, 1H); 7.02 (m, 1H) [C6 ring of indenyl]; 7.14 (dd, 1H); 5.80 (d, 1H) [C5 ring of indenyl]; 6.66 (m, 2H); 5.57 (m, 2H) [cyclopentadienyl ring]; 2.24 (s, 6H); 1.97 (s, 6H) [methyl].

EXAMPLE 12

Isopropylidene(cyclopentadienyl)(3-methylcyclopentadienyl)zirconium dichloride from the triethylstannyl-derivative in toluene (a) Synthesis of 2,2(cyclopentadienyl)(3-methyl-cyclopentadienyl)propane 50 g of the milled NaOH and 55 ml (550 mmol) of methylcyclopentadiene were suspended in 200 ml of THF and the mixture was stirred for 1 h. Then 60.2 ml (500 mmol) of 6,6-dimethylfulvene was added dropwise within 4 h and the mixture was stirred in additional 6 h. After that, the mixture treated by 200 ml of water and by 200 ml of diethyl ether. The organic layer was separated, washed by water and dried by CaCl$_2$. Then the solvent was removed in vacuo and the residue was distilled in vacuo (B.p. 79° C./0.07 Torr). 23.5 g of the product as a mixture of α- and β-methyl-isomers (7:9 by NMR of dilithio-derivative) was obtained (yield 25.2%). $^1$H-NMR (acetone-d6; 30° C.) d: 5.83–5.08 (mm, 5H) 2.27–2.05 (mm, 4H) 1.48–1.02 (s, 6H).

(b) Synthesis of isopropylidene(cyclopentadienyl) (3-methylcyclopentadienyl)zirconium dichloride 3.73 g (20 mmol) of 2,2-(cyclopentadienyl) (methylcyclopentadienyl)propane was dissolved in 100 ml of ether, cooled up to –20° C., and treated by 22 ml of 2.0M n-BuLi/pentane. The resulting suspension was allowed to warm to room temperature, then cooled up to –40° C., and treated with 12.06 g (50 mmol) of Et$_3$SnCl. Organic layer was separated, evaporated, and mixed with 50 ml of toluene. 4.66 g (20 mmol) of ZrCl$_4$ was added, and the mixture was stirred for 6 h under 80° C. Toluene was removed, crude product was recrystallased from THF. 3.24 g of the product was obtained (yield 85%).

EXAMPLE 13

Isopropylidene-bis (2-methyl-4-tertbutyl-cyclopentadienyl) zirconium dichloride from the trimethylstannylchloride in Et$_2$O 3.24 g (10 mmol) of 2,2-bis(2-methyl-4-t-butyl-cyclopentadienyl)propane was treated with 3.98 g (20 mmol) of trimethylstannylchloride diluted in 50 ml of Et$_2$O. The solution was decanted from LiCl precipitate, the solvent was removed and the residue was diluted with 40 ml of toluene. The resulting solution was treated with 2.33 g (10 mmol) of ZrCl$_4$ and the mixture was stirred until the ZrCl$_4$ was dissolved. Then the solvent was removed and the residual solid was recrystallized from heptane. A 1:1 rac-/meso- mixture of isopropylidene-bis(2-methyl-4-t-butyl-cyclopentadienyl) zirconium dichloride was obtained (yield 87%). Recrystallization from DME yields a 2:1 rac-/meso-mixture. $^1$H-NMR (CD$_2$Cl$_2$; 30° C.) rac-form δ: 6.29 (d, J=3.0 Hz, 2H); 5.51 (d, J=3.0 Hz, 2H) [cyclopentadienyl ring]; 2.16 (s, 6H, —CH$_3$ in ring); 1.91 (s, 6H, >C(CH$_3$)$_2$); 1.28 (s, 18H, —C(CH$_3$)$_3$). meso-form δ: 6.08 (d, J=3.0 Hz, 2H); 5.65 (d, 2H) [cyclopentadienyl ring]; 2.29 (s, 6H, —CH$_3$ in ring); 2.01, 1.88 (s, 2×3H, >C(CH$_3$)$_2$); 1.23 (s, 18H, —C(CH$_3$)$_3$). $^{13}$C-NMR (-"-) δ: 145.5; 118.2 [quat. C in ring]; 120.7; 106.2; 100.2 [tert. C in ring]; 37.0; 33.0; [>C<]; 30.1 [C(CH$_3$)$_3$]; 24.2 [>C(CH$_3$)$_2$].

EXAMPLE 14 rac-isopropylidene-bis(3-methyl-indenyl)zirconium dichloride from the triethylstannyl-derivative in toluene It was worked as in example 6 except that, instead of 2,2-bis(indenyl)propane, 20 mmol of the dilithium salt of 2,2-bis(3-methyl-indenyl)propane was used, and that the product was recrystallized from toluene. Pure rac-isopropylidene-bis(3-methyl-indenyl)zirconium dichloride was obtained. $^1$H-NMR (CD$_2$Cl$_2$, 30° C.) δ: 7.64 (d,2H); 7.42 (d,2H); 7.22 (m,2H); 6.96 (m,2H); 5.83 (s,2H); 2.30 (s,6H); 2.28 (s,6H).

EXAMPLE 15 rac-isopropylidene-bis(3-isopropyl-indenyl) zirconium dichloride from the triethylstannyl-derivative in toluene It was worked as in example 6 except that, instead of 2,2-bis(indenyl)propane, 20 mmol of the dilithium salt of 2,2-bis(3-isopropyl-indenyl)propane was used, and that the product was recrystallized from DME. Pure rac-isopropylidene-bis(3-isopropyl-indenyl)zirconium dichloride was obtained. $^1$H-NMR (toluene-d$_8$, 30° C.) δ: 7.34 (m.4H); 6.98 (m,2H); 6,69 (m,2H); 5.78 (s,2H); 3.14 (sept, 2H); 1.81 (s,6H); 1.20 (d,12H).

EXAMPLE 16 rac-isopropylidene-bis(3-tert-butyl-indenyl) zirconium dichloride from the triethylstannyl-derivative in toluene It was worked as in example 6 except that, instead of 2,2-bis(indenyl)propane, 20 mmol of the dilithium salt of 2,2-bis(3-tertbutyl-indenyl)propane was used, and that the product was recrystallized from DME. Pure rac-isopropylidene-bis(3-tertbutyl-indenyl)zirconium dichloride was obtained. $^1$H-NMR (CD$_2$Cl$_2$, 30° C.) δ: 7.75 (m.4H); 7.25 (dd,2H); 6,97 (dd,2H); 5.97 (s,2H); 2.33 (s,6H); 1.37 (s,18H).

EXAMPLE 17

Synthesis of 1,2-bis(1-trimethylsilyl-4,7-dimethyl-indenyl)ethane [EBDMI(TMS)$_2$]

103.8 g (331 mmol) of 1,2-bis(4,7-dimethyl-indenyl) ethane [EBDMIH$_2$] (Boulder, mixture of double bonds positional isomers) were slurred in 680 mL of THF in a 1 L flask equipped with stirring bar. This suspension was added in small aliquots over 30 minutes at room temperature in a 2 L flask equipped with reflux condenser, thermometer and mechanical stirrer, containing 29.48 g of KH (735 mmol) and 205 mL of THF. The reaction was slightly exothermic (T max. 43° C.) with evolution of hydrogen. At the end of the addition the so obtained suspension was stirred for 2 h, obtaining a dark green solution. In a second 2 L flask equipped with thermometer, mechanical stirrer and dropping funnel were placed 93.2 mL of Me$_3$SiCl (734 mmol) and 210 mL of THF. The dark green solution of the potassium salt was added dropwise (2 h, slightly exothermic reaction, T max. 30° C.) and at the end of the addition the mixture was stirred for 44 h, obtaining a brown-orange milk. The reaction was monitored by NMR (40 mg dissolved in CDCl$_3$) and GC. After 16 h the reaction was complete. After 44 h the mixture was treated with water (200 mL) while stirring, and then NaCl to induce phase separation. The organic layer was dried over Na$_2$SO$_4$, filtered and brought to dryness. 142.8 g of a light brown solid was obtained (yield 94.3%).

EXAMPLE 18

Separation of rac- and meso-1,2-bis(1-trimethylsilyl-4,7- dimethyl-indenyl)ethane 105.3 g of EBDMI(TMS)$_2$ prepared as in example 17 were slurred in 0.5 L of pentane and filtered on a G4 frit. The filtrate (dark red) brought to dryness yields 60.3 g of dark red product. $^1$H NMR (C$_2$D$_2$Cl$_4$ 120° C.): rac/meso ca. 9/1. The ochre residue was continuously extracted with hexane. The product crystallizes in the receiving flask. After cooling to room temperature overnight at room temperature, the mother liquor was eliminated and the crystalline product was brought to dryness in vacuo. 37.4 g of product were obtained. The $^1$H-NMR analysis (C$_2$D$_2$Cl$_4$ 120° C.) shows the presence of a single diastereoisomer. This compound was recrystallized from Et$_2$O and one crystal analyzed by X-rays diffraction resulted to be the meso isomer.

EXAMPLE 19

Synthesis of a 11.5:1 rac/meso-ethylene-bis(4,7-dimethyl-indenyl)zirconium dichloride mixture 2.28 g (5.0 mmol) of the pentane-soluble fraction of EBDMI(TMS)$_2$ prepared as in example 18, 21 mL of CH$_2$Cl$_2$ and 1.16 g of ZrCl$_4$ (5.0 mmol) were placed under nitrogen in a 100 mL tube equipped with magnetic stirrer. The mixture was stirred for 3 h at room temperature and a yellow-brown suspension was obtained. The reaction was stopped by bringing to dryness. A yellow-brown free-flowing powder was obtained. The NMR analysis shows the presence of rac-EBDMIZrCl$_2$ and about 10% meso-form plus unidentified impurities. The powder was placed on a frit and washed with ethanol (5 mL) and Et$_2$O (5×2 mL). After drying in vacuo, 1.23 g (52%) of orange powder were obtained. $^1$H NMR analysis shows the presence of 92% rac-EBDMIZrCl$_2$ and 8% meso-EBDMIZrCl$_2$.

EXAMPLE 20

Synthesis of meso-ethylene-bis(4,7-dimethyl-indenyl)zirconium dichloride 37.4 g (81 mmol) of the meso-EBDMI(TMS)$_2$ prepared in example 18, 200 mL of CH$_2$Cl$_2$ and 19.0 g of ZrCl$_4$ (81 mmol) were placed under nitrogen in a 500 mL flask equipped with stirring bar. The mixture was stirred for 4 h at room temperature and a dark green suspension was obtained. The reaction was stopped by removing the solvent in vacuo: a dark green free-flowing powder was obtained. The powder was placed on a frit and washed with THF until the washing was bright yellow (75×4 mL). After drying in vacuo, 31.3 g (80%) of light yellow powder were obtained. $^1$H NMR analysis shows the presence of pure meso-EBDMIZrCl$_2$

EXAMPLE 21

Synthesis of 2,2-bis(1-trimethylsilyl-3-indenyl) propane 3.3 g of 2,2-bis(3-indenyl)propane (20511/46, MW 272.39, 12.11 mmol) and 50 m of THF in a 100 mL flask were cooled to −70° C. while stirring. 17 mL of a 1.6 M solution of BuLi (27.2 mmol) in hexane were added dropwise. At the end of the addition, the reaction mixture was allowed to warm to room temperature and stirred for 1 h. The solution was cooled again to −70° C. and 3.4 mL of Me$_3$SiCl (MW 108.64, d 0.856, 26.8 mmol) were added. At the end of the addition, the reaction mixture was allowed to warm to room temperature and stirred for 2 h. Water is then added, the organic layer is separated and the water layer extracted twice with Et$_2$O, all organic phases were combined and dried over MgSO$_4$, then filtered and all volatiles removed in vacuo. 4.8 g (95%) of a mixture of rac/meso 2,2-bis(1-trimethylsilyl-3-indenyl)propane was obtained. $^1$H NMR (200 MHz, C$_2$D$_2$Cl$_4$, 120° C., referenced to the peak of residual C$_2$HDCl$_4$ at 5.75 ppm): 7.1–7.3 (m, 4H, C$_6$ ring), 6.75–6.95 (m, 4H, C$_6$ ring), 6.3–6.4 (br s, 2H, C$_5$ ring), 3.2–3.3 (m, 2H, C$_5$ ring), 1.64, 1.62 (2 s, 6H, bridge methyls), −0.15, −0.17 (2 s, 18H, TMS methyls).

Polymerizations

Methylalumoxane (MAO)

A commercial product (WITCO, MW 1400) was used in a 30% by weight solution in toluene. After removal of the volatile fractions in vacuo, the solid glassy material was crushed and finally treated in vacuo (0.1 mm Hg) for 4–6 hours at a temperature of 40–50° C., to give a white powder.

Modified Methylalumoxane (M-MAO)

A commercial product (ALBEMARLE) was used as such in a solution (62 of Al/l) in Isopar C.

EXAMPLE 22

Ethylene polymerization with the rac/meso mixture of ethylene-bis(indenyl)zirconium dichlorides from Example 1

Into a 1 litre Büchi autoclave having glass body, provided with jacket, elicoidal stirrer and thermoresistance, and joined to a thermostat to control the temperature, washed with a solution of triisobutyl aluminum in n-hexane and dried in warm under anhydrous nitrogen stream, 0.4 l of n-hexane (purified by passage on alumina columns) were introduced under nitrogen. The temperature was raised to a value of 7–8° C. below the polymerization temperature and the nitrogen was substituted by ethylene. The catalyst solution was prepared as follows. To a quantity of a MAO solution in toluene (10 mg/ml toluene) containing 2 mmol aluminum, 0.165 of a toluene solution of the ethylene-bis (indenyl)zirconium dichloride obtained in Example 1 (0.6 mg/ml toluene) was added and the whole was kept at room temperature for 10 minutes. The solution was injected into the autoclave by a slight ethylene overpressure. The temperature was then raised to 50° C. and kept constant for all the duration of the polymerization. The pressure was raised to 4 ata and kept constant by supplying ethylene. The reaction was then ceased by removing the ethylene overpressure and injecting a little quantity of methanol. The polymer obtained was dried in oven at 60° C. under nitrogen stream. 14.3 g of polymer was obtained having M$_w$/M$_n$=4.7.

EXAMPLE 23

Propylene polymerization with isopropylidene (cyclopentadienyl)(indenyl)zirconium dichloride from Example 10

480 g of propylene were charged in a 1.4 l jacketed stainless-steel autoclave, equipped with magnetically driven stirrer, 35-ml stainless-steel vial and thermoresistance, connected to a thermostat for temperature control, previously dried at 70° C. in a stream of propylene. The autoclave was then thermostatted at 40° C. 4.6 ml of the M-MAO solution in isopar-C was used to dissolve 4 mg of Me$_2$C(Cp)(Ind) ZrCl$_2$ prepared as described in example 10 (Al/Zr=1000 molar), the resulting red-brown solution was stirred 10 min at room temperature and then injected in the autoclave by means of propylene pressure through the stainless-steel vial, the temperature rapidly raised to 50° C. and the polymerization carried out at constant temperature for 1 hour. After venting the unreacted monomer, 42 g of a viscous, clear product were obtained, which had an average degree of polymerization (as measured by $^1$H NMR) of 41, and end groups of the vinylidene type.

EXAMPLE 24

Propylene polymerization with isopropylidene (cyclopentadienyl)(3-methylcyclopentadienyl) zirconium dichloride from Example 12

It was worked according to the procedure described in Example 23, but using 3.77 ml of the M-MAO solution, and 1 mg of the metallocene prepared in Example 12. The polymerization was carried out at 50° C. for 1 hour. After venting the unreacted monomer, 14 g of a viscous, clear product were obtained, which had an average degree of polymerization (as measured by $^1$H NMR) of 20, and end groups of the vinylidene type.

We claim:

1. A process for the preparation of a bridged metallocene compound in the racemic or meso isomeric form, or as a mixture of the racemic and meso isomeric forms, said process comprising the following steps:

(a) reacting a ligand having two substituted and bridged cyclopentadienyl groups with a compound able to form a delocalized anion on each of the cyclopentadienyl, thus obtaining the corresponding anion;

(b) reacting the double anion with a compound of formula ZR$_3$Q or (ZR$_2$)$_m$Q$_2$, wherein Z is a silicon, germanium or tin atom, R is a hydrocarbon group containing from 1 to 10 carbon atoms, Q is a halogen atom, m is 1 or 2, thus obtaining a mixture of the racemic and isomeric forms of a Z-substituted bridged bis-cyclopentadienyl ligand of formula (II):

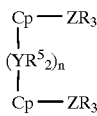

(II)

or of formula (III):

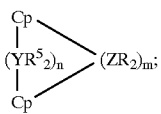

(III)

wherein each Cp is a substituted cyclopentadienyl ring; the R$^5$ substituents, same or different, are C$_1$–C$_{20}$ alkyl radicals, C$_3$–C$_{20}$-cycloalkyl radicals, C$_2$–C$_{20}$ alkenyl radicals, C$_6$–C$_{20}$ aryl radicals, C$_7$–C$_{20}$ alkylaryl radicals, or C$_7$–C$_{20}$ arylalkyl radicals, and moreover two substituents R$^5$ can form a cycle comprising from 4 to 8 carbon atoms;

Y is a carbon, silicon, or germanium atom; and n is an integer comprised between 1 and 4; and m and R are defined above, and further wherein when Y is a silicon atom, Z is a germanium atom or tin atom;

and further wherein when Y is a germanium atom, Z is a tin atom;

(c) if desired, separating at least part of one of the isomeric forms of the Z-substituted bridged bis-cyclopentadienyl ligand; and (d) converting the Z-substituted breidged bis-cyclopentadienyl ligand into the desired product through reaction with a transition metal compound, the reaction being carried put in a liquid dispersant which does not coordinate with the transition metal compound.

2. The process according to claim 1, wherein the bridged bis-cyclopentadienyl ligand has the formula (I):

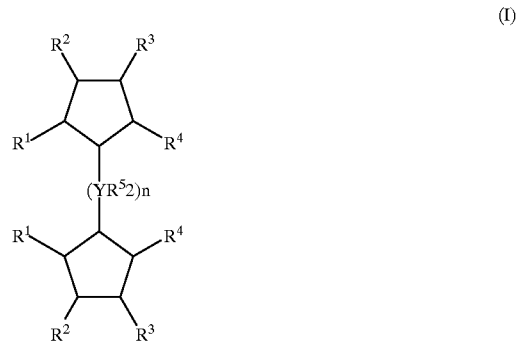

(I)

wherein, on each cyclopentadienyl group, the R$^1$, R$^2$, R$^3$ and R$^4$ substituents, same or different, are C$_1$–C$_{20}$ alkyl radicals, C$_3$–C$_{20}$ cycloalkyl radicals, C$_2$–C$_{20}$ alkenyl radicals, C$_6$–C$_{20}$ aryl radicals, C$_7$–C$_{20}$ alkylaryl radicals or C$_7$–C$_{20}$ arylalkyl radicals and can contain Si or Ge atoms, and moreover two of the R$^1$, R$^2$, R$^3$ and R$^4$ substituents adjacent on the same cyclopentadienyl ring can form a cycle comprising from 5 to 8 carbon atoms, with the proviso that, in at least one cyclopentadienyl group, R$^1$ is different from R$^4$ or R$^2$ is different from R$^3$;

Y is a carbon, silicon or germanium atom;

the R$^5$ substituents, same or different, are C$_1$–C$_{20}$ alkyl radicals, C$_3$–C$_{20}$ cycloalkyl radicals, C$_2$–C$_{20}$ alkenyl radicals, C$_6$–C$_{20}$ aryl radicals, C$_7$–C$_{20}$ alkylaryl radicals or C$_7$–C$_{20}$ arylalkyl radicals, and moreover two substituents R$^5$ can form a cycle comprising from 4 to 8 carbon atoms;

n is an integer comprised between 1 and 4.

3. The process according to claim 2, wherein in the compound of formula (I) n is 1 or 2.

4. The process according to claim 1, wherein the compound able to form a delocalized anion is selected between:

organometallic compounds of alkali or earth-alkali metals;

metal hydrides;

alkali or earth-alkali metals;

amides of alkali or earth-alkali metals.

5. The process according to claim 4, wherein the organometallic compounds of alkali or earth-alkali metals are alkyl-lithium compounds.

6. The process according to claim 5, wherein the alkyl-lithium compounds are selected between methyl-lithium or n-butyl-lithium.

7. The process according to claim 1, wherein in the compound of formula $ZR_3Q$ or $(ZR_2)_mQ_2$, Z is a silicon atom.

8. The process according to claim 1, wherein in the compound of formula $ZR_3Q$ or $(ZR_2)_mQ_2$, Q is a chlorine atom.

9. The process according to claim 1, wherein in the compound of formula $ZR_3Q$ or $(ZR_2)_mQ_2$, R is an alkyl group containing from 1 to 3 carbon atoms.

10. The process according to claim 1, wherein the transition metal compound that can be used in the reaction of step (d) is selected between the compounds of transition metals belonging to the group 3, 4, 5 or 6 or to the Lanthanides or Actinides group of the Periodic Table of the Elements (new IUPAC version).

11. The process according to claim 10, wherein the transition metal compound is a compound of formula $MX_4$, wherein M is a titanium, zirconium or hafnium atom and X is an halogen atom.

12. The process according to claim 11, wherein the compound of formula $MX_4$ is selected between titanium tetrachloride, zirconium tetrachloride and hafnium tetrachloride.

13. A bridged bis-cyclopentadienyl ligand of formula (II):

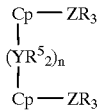

(II)

or of formula (III):

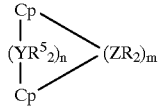

(III)

wherein each Cp is a substituted cyclopentadienyl ring, and $R^5$, Y, and n are defined in claim 2, m is 1 or 2, and R is an a hydrocarbon containing from 1 to 10 carbon atoms, and Z is a silicon, germanium, or tin atom, and further wherein when Y is a silicon atom, Z is germanium or tin atom, and further wherein when Y is a germanium atom, Z is a tin atom, in its racemic or meso isomeric form.

14. The bridged bis-cyclopentadienyl ligand according to claim 13, wherein Z is a silicon atom.

15. A bridged bis-cyclopentadienyl ligand selected from the group consisting of 1,2-bis(1-trimethylsilyl-indenyl) ethane, 1,2-bis(1-trimethylsilyl-4,7-dimethyl-indenyl) ethane and 2,2-bis(1-trimethylsilyl-indenyl)propane.

16. The process according to claim 1, wherein the bridged bis-cyclopentadienyl ligand has formula (I):

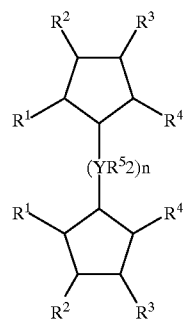

(I)

wherein, on each cyclopentadienyl group, the $R^1$, $R^2$, $R^3$, and $R^4$ substituents, same or different, are $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ arylalkyl radicals, or $C_7$–$C_{20}$ arylalkyl radicals and can contain Si or Ge atoms, and moreover two of the $R^1$, $R^2$, $R^3$, and $R^4$ substituents adjacent on the same cyclopentadienyl ring can form a cycle comprising from 5 to 8 carbon atoms, with the proviso that, in at least one cyclopentadienyl group, $R^1$ is different from $R^4$, or $R^2$ is different from $R^3$;

Y is a carbon, silicon, or germanium atom;

the $R^5$ substituents, same or different, are H, $C_1$–$C_{20}$ alkyl radicals, $C_3$–$C_{20}$ cycloalkyl radicals, $C_2$–$C_{20}$ alkenyl radicals, $C_6$–$C_{20}$ aryl radicals, $C_7$–$C_{20}$ alkylaryl radicals, or $C_7$–$C_{20}$ arylalkyl radicals and can contain Si or Ge atoms, and moreover two $R^5$ substituents can form a cycle comprising from 5 to 8 carbon atoms; and n is an integer comprised between 1 and 4.

17. The process according to claim 16, wherein in the compound of formula (I) n is 1 or 2.

18. The process according to claim 16, wherein the compound able to form a delocalized anion is selected between:

organometallic compounds of alkali or earth-alkali metals;

metal hydrides;

alkali or earth-alkali metals amides of alkali or earth-alkali metals.

19. The process according to claim 18, wherein the organometallic compounds of alkali or earth-alkali metals are alkyl-lithium compounds.

20. The process according to claim 19, wherein the alkyl-lithium compounds are selected between methyl-lithium or n-butyl lithium.

21. The process according to claim 16, wherein in the compound of formula $ZR_3Q$ or $(ZR_2)_mQ_2$, Z is a silicon atom.

22. The process according to claim 16, wherein in the compound of formula $ZR_3Q$ or $(ZR_2)_mQ_2$, Q is a chlorine atom.

23. The process according to claim 16, wherein in the compound of formula $ZR_3Q$ or $(ZR_2)_mQ_2$, R is an alkyl group containing from 1 to 3 carbon atoms.

24. The process according to claim 16, wherein the transition metal compound that can be used in the reaction of step (d) is selected between the compounds of transition metals belonging to the group 3, 4, 5 or 6 or to the Lanthanides or Actinides group of the Periodic Table of the Elements (new IUPAC version).

25. The process according to claim 24, wherein the transition metal compound is a compound of formula $MX_4$, wherein M is a titanium, zirconium, or hafnium atom and X is a halogen atom.

26. The process according to claim 25, wherein the compound of formula $MX_4$, is selected between titanium tetrachloride, zirconium tetrachloride, and hafnium tetrachloride.

27. A bridged bis-cyclopentadienyl ligand of formula (II):

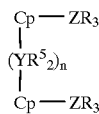
(II)

or of formula (III):

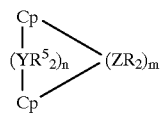
(III)

wherein each Cp is a substituted cyclopentadienyl ring, and $R^5$, Y, and n are defined in claim 16, m is 1 or 2, and R is an alkyl group containing from 1 to 10 carbon atoms, and Z is a silicon, germanium, or tin atom, and further wherein when Y is a silicon atom, Z is germanium or tin atom, and further wherein when Y is a germanium atom, Z is a tin atom, in its racemic or meso isomeric form.

28. The bridged bis-cyclopentadienyl ligand according to claim 27, wherein Z is a silicon atom.

29. A process for the preparation of a bridged metallocene compound in the racemic or meso isomeric form, or as a mixture of the racemic and meso isomeric forms, said process comprising the following steps:

(a) reacting a ligand having two substituted and bridged cyclopentadienyl groups with a compound able to form a delocalized anion on each of the cyclopentadienyl, thus obtaining the corresponding anion;

(b) reacting the double anion with a compound of formula $ZR_3Q$ or $(ZR_2)_m Q_2$, wherein Z is a silicon, germanium or tin atom, R is a hydrocarbon group containing from 1 to 10 carbon atoms, Q is a halogen atom, m is 1 or 2, thus obtaining a mixture of the racemic and isomeric forms of a Z-substituted bridged bis-cyclopentadienyl ligand of formula (II):

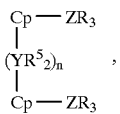
(II)

or of formula (III):

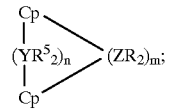
(III)

wherein each Cp is a substituted cyclopentadienyl ring; the $R^5$ substituents, same or different, are hydrogen, $C_1$–$C_{20}$ alkyl radicals, $C_3$–$C_{20}$-cycloalkyl radicals, $C_2$–$C_{20}$ alkenyl radicals, $C_6$–$C_{20}$ aryl radicals, $C_7$–$C_{20}$ alkylaryl radicals, or $C_7$–$C_{20}$ arylalkyl radicals, and moreover two substituents $R^5$ can form a cycle comprising from 4 to 8 carbon atoms;

Y is a carbon, silicon, or germanium atom; and n is an integer comprised between 1 and 4; and m and R are defined above;

and further wherein when Y is a silicon atom, Z is a germanium atom or tin atom;

and further wherein when Y is a germanium atom, Z is a tin atom;

(c) if desired, separating at least part of one of the isomeric forms of the Z-substituted bridged bis-cyclopentadienyl ligand; and (d) converting the Z-substituted bridged bis-cyclopentadienyl ligand into the desired product through reaction with a transition metal compound, the reaction being carried put in a liquid dispersant which does not coordinate with the transition metal compound.

* * * * *